United States Patent
Berend et al.

(10) Patent No.: US 9,833,572 B2
(45) Date of Patent: Dec. 5, 2017

(54) MODULAR DUAL CHAMBER SYRINGE SYSTEM

(71) Applicants: Michael E. Berend, Indianapolis, IN (US); Kurt M. Kramer, Indianapolis, IN (US)

(72) Inventors: Michael E. Berend, Indianapolis, IN (US); Kurt M. Kramer, Indianapolis, IN (US)

(*) Notice: Subject to any disclaimer, the term of this patent is extended or adjusted under 35 U.S.C. 154(b) by 219 days.

(21) Appl. No.: 14/976,627

(22) Filed: Dec. 21, 2015

(65) Prior Publication Data

US 2016/0206818 A1   Jul. 21, 2016

Related U.S. Application Data

(60) Provisional application No. 62/104,950, filed on Jan. 19, 2015.

(51) Int. Cl.
| | | |
|---|---|---|
| *A61M 31/00* | (2006.01) | |
| *A61M 37/00* | (2006.01) | |
| *A61M 5/19* | (2006.01) | |
| *A61M 5/315* | (2006.01) | |
| *A61M 5/00* | (2006.01) | |
| *A61M 5/32* | (2006.01) | |
| *A61M 5/31* | (2006.01) | |

(52) U.S. Cl.
CPC .............. *A61M 5/19* (2013.01); *A61M 5/002* (2013.01); *A61M 5/3129* (2013.01); *A61M 5/31596* (2013.01); *A61M 5/3202* (2013.01); *A61M 2005/3142* (2013.01)

(58) Field of Classification Search
CPC .... A61M 5/002; A61M 5/19; A61M 5/31596; A61M 5/3202; A61M 2005/3142; A61M 5/3129
USPC ........................................................ 604/506
See application file for complete search history.

(56) References Cited

U.S. PATENT DOCUMENTS

| | | | |
|---|---|---|---|
| 3,477,432 A | | 11/1969 | Shaw |
| 5,053,019 A | | 10/1991 | Duffy |
| 5,364,369 A | * | 11/1994 | Reynolds .............. A61J 1/2089 604/187 |
| 5,569,193 A | | 10/1996 | Hofstetter et al. |

(Continued)

*Primary Examiner* — Jason Flick
(74) *Attorney, Agent, or Firm* — Bassam S. Nader; Brannon Sowers & Cracraft PC

(57) ABSTRACT

The present disclosure provides a modular, connectable, dual chamber syringe system that can be used to mix, dispense and/or inject multiple materials sequentially or concurrently. The dual chamber syringe system may be prefilled in advance with different materials, e.g., multiple medicaments, and prepackaged, and is capable of being removed from the packaging and being used immediately, such as in a medical setting. In one illustrative embodiment, the dual chamber syringe system includes a design with the following arrangement of the main components: hypodermic needle—first container with female threaded end—male threaded cap—female threaded cap—second container with male threaded end—plunger. In a second illustrative embodiment, the dual chamber syringe system includes a design with the following arrangement of the main components: hypodermic needle—first container with female threaded end—membrane—membrane—second container with male threaded end—plunger.

20 Claims, 7 Drawing Sheets

(56) References Cited

U.S. PATENT DOCUMENTS

| | | | |
|---|---|---|---|
| 5,637,087 | A | 6/1997 | O'Neil et al. |
| 5,779,668 | A | 7/1998 | Grabenkort |
| 5,971,953 | A | 10/1999 | Bachynsky |
| 6,027,472 | A | 2/2000 | Kriesel et al. |
| 6,132,400 | A | 10/2000 | Yang |
| 6,224,568 | B1 | 5/2001 | Morimoto |
| 7,311,692 | B2 | 12/2007 | Kato |
| 8,517,983 | B2 | 8/2013 | Kakiuchi et al. |
| 8,728,054 | B2 | 5/2014 | Schulhof |
| 2004/0236273 | A1 | 11/2004 | Tanaka et al. |
| 2006/0189943 | A1 | 8/2006 | Kato |
| 2010/0228121 | A1 | 9/2010 | Kazuhiro |
| 2010/0318063 | A1 | 12/2010 | Soll |
| 2012/0325367 | A1* | 12/2012 | Mathys .............. A61B 17/8833 141/18 |

* cited by examiner

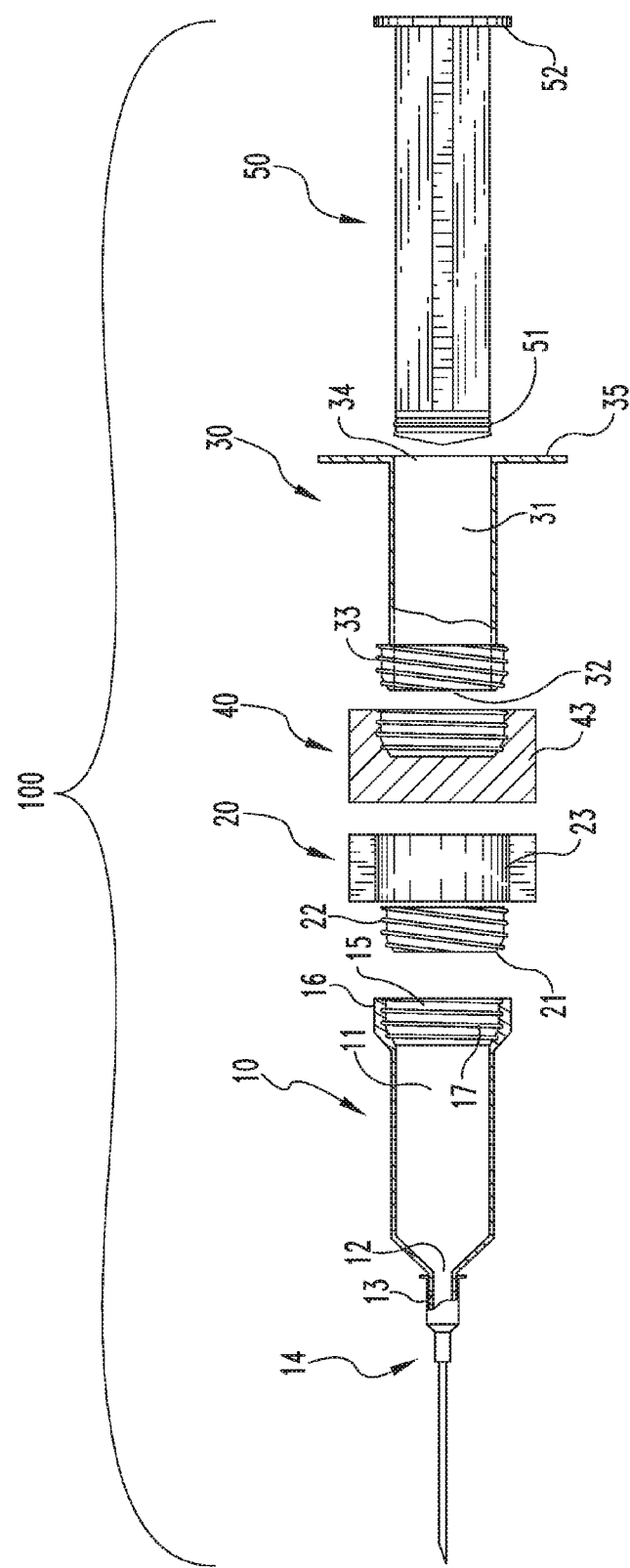

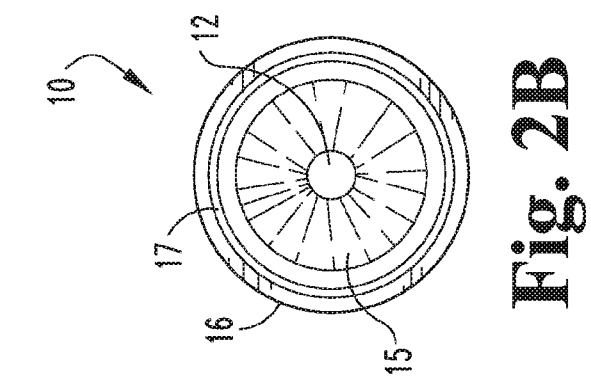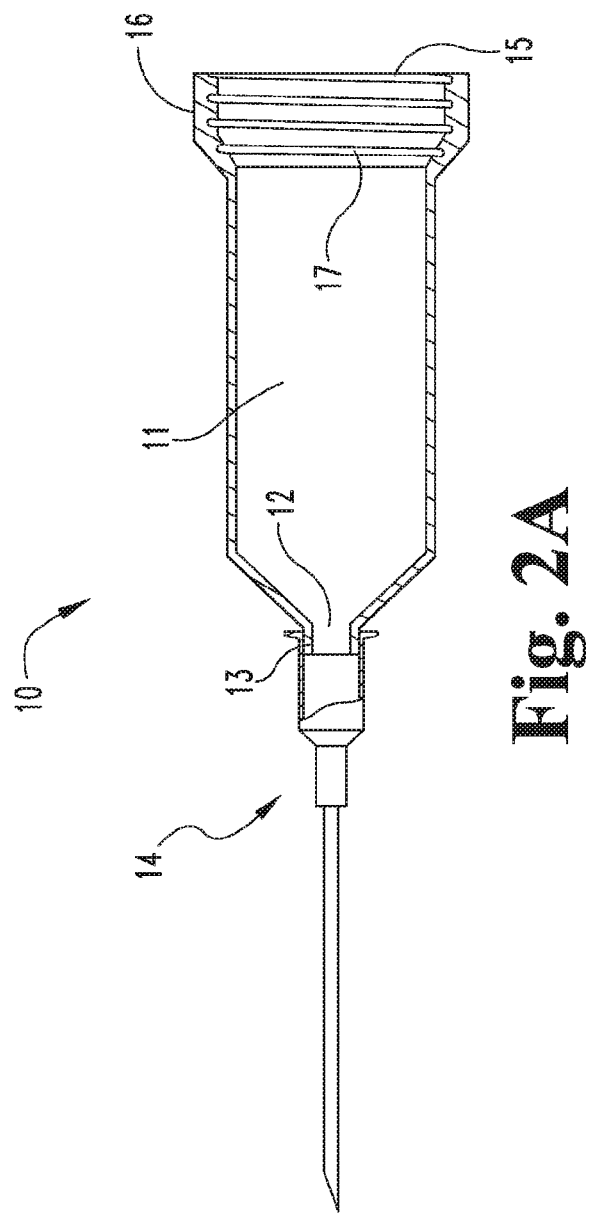

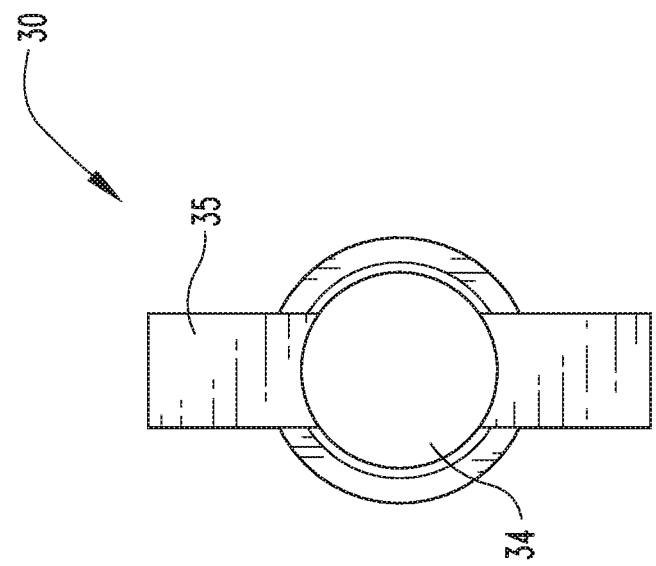
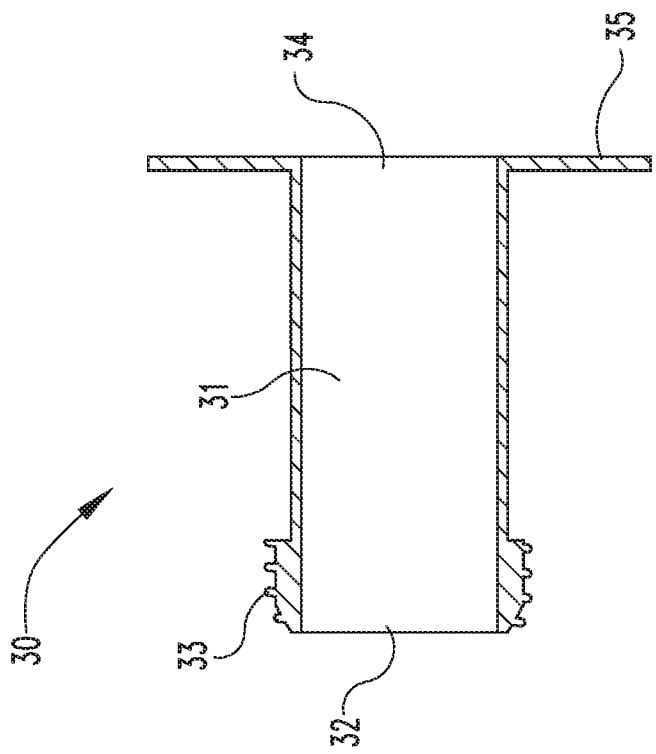

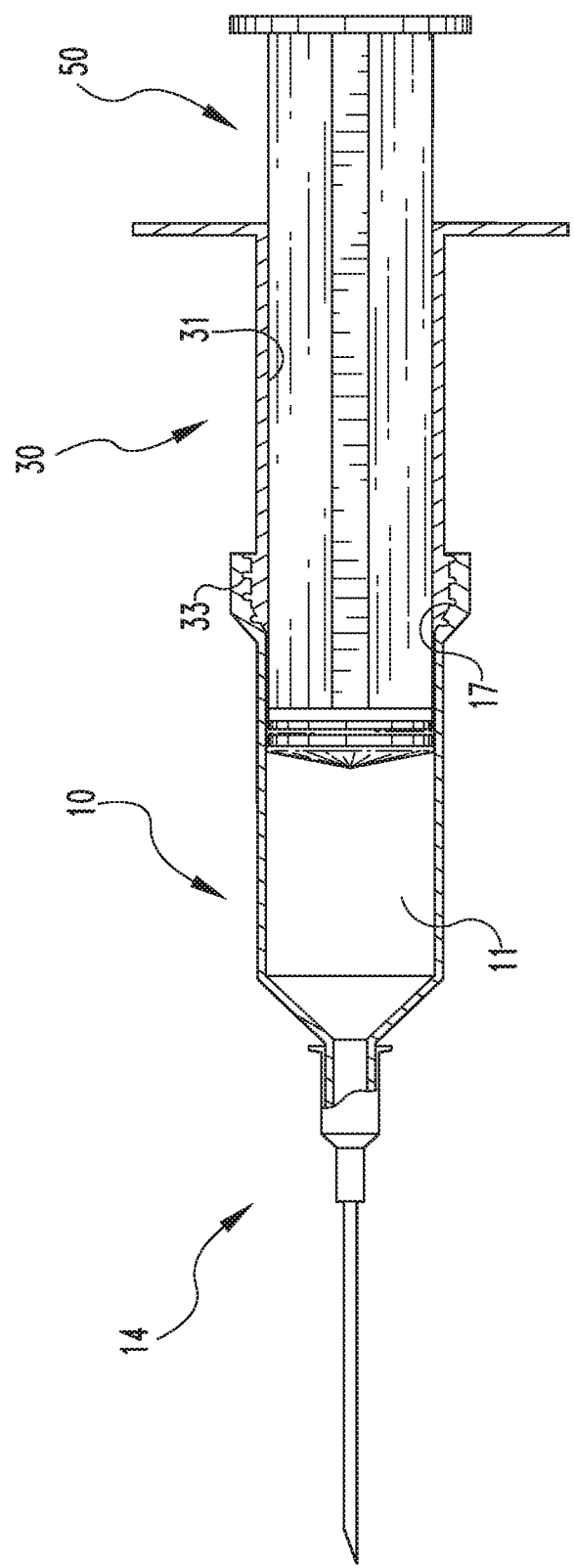

MODULAR DUAL CHAMBER SYRINGE SYSTEM

CROSS-REFERENCE TO RELATED APPLICATIONS

This application claims priority under 35 USC §119(e) to U.S. Provisional Application Ser. No. 62/104,950, filed Jan. 19, 2015, the entire disclosure of which is incorporated herein by reference.

FIELD OF INVENTION

The present disclosure relates to a dual barrel syringe system. In particular, the present invention is related to a syringe system for mixing one or more materials, e.g., medicaments, immediately prior to or concurrently with dispensing. The present invention also relates to a syringe system that can be used to mix and/or dispense multiple materials sequentially or concurrently, and for mixing multiple materials at the time of use. The present invention also relates to a syringe system that may be prefilled in advance with different materials, e.g., multiple medicaments, and prepackaged, and is capable of being removed from the packaging and being used immediately, such as in a medical setting.

BACKGROUND OF INVENTION

Syringes or syringe-like dispensers are commonly used for dispensing and/or injecting various fluids/materials, e.g., for administering medicaments in a medical setting. Moreover, most syringes are designed for dispensing or injecting a single fluid/material. However, there is an ever increasing need to dispense two different fluids/materials that need to be isolated from each other during storage but mixed immediately prior to or concurrently with their use. Dispensing of fluids/materials in such a manner is required in numerous applications, especially in medical settings.

Certain medications become chemically unstable and undergo chemical transformation over a period of time when admixed, thus precluding storage while mixed, and requiring extra preparation effort and additional time prior to administration, e.g., at the time of treatment or carrying out a surgical procedure. For example, some pharmaceutical preparations, such as injectable solutions or suspensions of a drug, are not sufficiently stable to accommodate prolonged storage prior to use; however, the components of the solution or suspension may have adequate stability if the components are stored separately prior to being mixed for use. As an example, a mixture of lidocaine and corticosteroid, commonly used in certain medical procedures, begins to deteriorate in less than 24 hours when combined in a single chamber.

It is therefore desirable to introduce a simple, modular syringe system that is capable of being prefilled with multiple materials in isolation from each other, and prepackaged for storage, such that when the need arises the system can be immediately removed from the packaging and used without the need for a complicated operation. Such a system would be particularly useful in the reduction of the work of those engaged in medical practice such as doctors, nurses, and medical technicians.

Many syringes and syringe systems have been disclosed to-date that attempt to solve some of the above needs. Examples include U.S. Pat. No. 3,477,432 to Shaw; U.S. Pat. No. 5,053,019 to Duffy; U.S. Pat. No. 5,364,369 to Reynolds; U.S. Pat. No. 5,569,193 to Hofstetter et al.; U.S. Pat. No. 5,637,087 to O'Neil et al.; U.S. Pat. No. 5,779,668 to Grabenkort; U.S. Pat. No. 5,971,953 to Bachynsky; U.S. Pat. No. 6,027,472 to Kriesel et al.; U.S. Pat. No. 6,132,400 to Waldenburg; U.S. Pat. No. 6,224,568 to Morimoto et al.; U.S. Pat. No. 6,468,250 to Yang; U.S. Pat. No. 7,311,692 to Kato et al.; U.S. Pat. No. 8,517,983 to Kakiuchi et al; and, U.S. Pat. No. 8,728,054 to Schulhof. However, these syringes and syringe systems suffer from having intricate designs and highly complex features, making them costly to produce and/or purchase, and potentially cumbersome to use. Accordingly, there is an ongoing need for simple and versatile syringe-like dispenser systems that are capable of storing multiple materials and mixing such materials immediately prior to use and/or delivering such materials in an immediate sequential manner.

SUMMARY OF INVENTION

In one embodiment, the present disclosure provides a modular dual chamber (or dual barrel) syringe system designed to allow prepackaging and storage of more than one injectable medication in two separate chambers. In one aspect, prepackaging of the medications is accomplished under sterile conditions; thus, the medications are practically ready for use, with minimal preparation, simply by removing the sterile contents from the packaging and combining the two chambers together, as will become clear in the discussion below. In another aspect, use of the system herein results in reduction of time spent preparing the injectables, allowing for more direct patient contact and increased patient volume. Furthermore, use of the system herein results in reduction of the potential for contamination of the injectables, thus decreasing risk of infection. Moreover, use of the system herein results in reduction of the required storage space for injectable supplies. It also facilitates precise dosage administration, and streamlining of medical supply ordering. All of the foregoing help improve patient care, save time, and reduce costs.

In another embodiment, described herein is a modular, connectable, dual chamber syringe system comprising two separate containers, which can contain different medications each, with capability to be connected to mix the medications during administration. In one aspect, one of the containers includes a female threaded end and the other container includes a male threaded end, wherein the threaded ends are simply screwed together to connect the two containers.

In another embodiment, described herein is a modular, connectable, dual chamber syringe system comprising two separate containers, each container partially resembling a syringe. The system includes a first, plungerless container with a female threaded end, and a second, plungered container with a male threaded end.

In another embodiment, described herein is a modular, connectable, dual chamber syringe system comprising two separate containers with threaded ends as described in the preceding paragraph, wherein the system includes appropriately threaded caps for sealing each of the containers until the need arises to connect them for use. Alternatively, instead of threaded caps, the system includes any of a variety of other suitable sealing methods known in the art for sealing of the containers. Thus, illustratively, sealing of the containers may be accomplished by using membranes, as is discussed below.

In another embodiment, the modular, connectable, dual chamber syringe system herein includes a design with the following arrangement of the main components: hypodermic needle—first container with female threaded end—male threaded cap—female threaded cap—second container with male threaded end—plunger. Alternatively, in the case where membranes are used to seal the containers, the design may have the following arrangement of components: hypodermic needle—first container with female threaded end—membrane—membrane—second container with male threaded end—plunger.

In another embodiment, the modular, connectable, dual chamber syringe system herein includes a kit. In one aspect, the kit includes the main components in the preceding paragraphs, wherein the first container is already pre-charged with one medication and sealed with a male threaded cap or alternatively with a membrane and a needle shield, the second container is already pre-charged with another medication and sealed with a female threaded cap or alternatively with a membrane and the plunger, and the components are packaged under sterile conditions. In an alternative aspect, instead of the needle/needle shield, the first container may be capped at the tip with a tip cap. In yet another alternative aspect, it is contemplated herein that the two pre-charged and sealed containers may be packaged separately.

In another embodiment, disclosed herein is a method of use of the modular, connectable, dual chamber syringe system described herein. This method comprises the steps of removing the components from the pre-packaged kit described in the preceding paragraph, unscrewing the threaded caps off their respective containers if such caps have been used to seal the containers, connecting the containers by screwing them together resulting in mixing of the medications, and injecting into a patient by pushing the plunger. Alternatively, if membranes have been used to seal the containers instead of threaded caps, then connecting the containers by screwing them together would rupture the membranes resulting in mixing of the medications, which are then injected into a patient by pushing the plunger.

It is to be understood that, as used herein, the terms "medication," "medicament," "injectable," and other similar terms may refer to a solution, a suspension, an emulsion, a gel, or similar media commonly used in the medical field, comprising a single drug or active ingredient or a multiplicity of drugs or active ingredients.

Other advantages and features of the present invention will become apparent from the following detailed description, the claims, and the accompanying drawings.

DESCRIPTION OF DRAWINGS

The foregoing summary, as well as the following detailed description of the preferred embodiments of the invention, will be better understood when read in conjunction with the accompanying figures, in which:

FIG. 1 is a partially exploded, longitudinal cross-sectional view of the dual chamber syringe system in accordance with the invention;

FIG. 2A is a longitudinal cross-sectional view of the first chamber with the needle attached;

FIG. 2B is a cross-sectional view of the first chamber looking down the back end;

FIG. 4A is a longitudinal cross-sectional view of the second chamber;

FIG. 4B is a cross-sectional view of the second chamber looking down the front end;

FIG. 7 is a longitudinal cross-sectional view of the assembled dual chamber syringe system showing the plunger pushed all the way through the second chamber and partially into the first chamber.

DETAILED DESCRIPTION

Figure 3A:
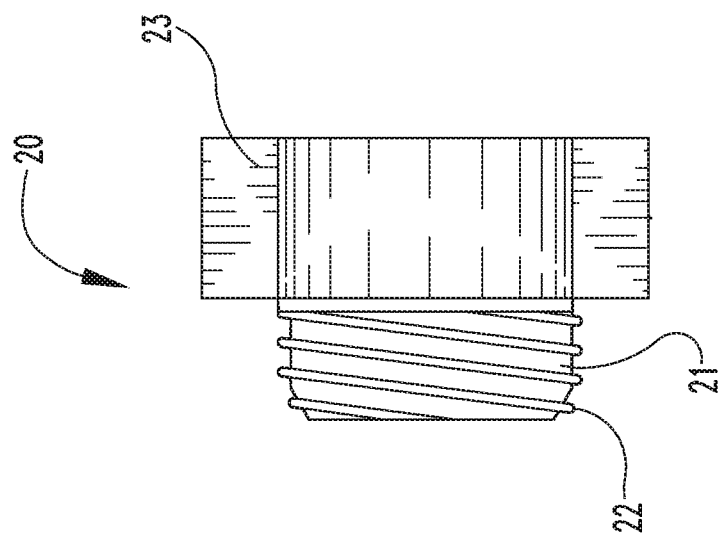
FIG. 3A is a longitudinal cross-sectional view of the male end cap of the first chamber.

Before the present details of the invention are disclosed and described, it is to be understood that this invention is not limited to the specific components, methods, and implementation, or to the precise arrangements and instrumentalities shown, as such may, of course, vary while remaining within the scope and spirit of the invention. It is also to be understood that the terminology used herein is for the purpose of describing particular implementations only, and to assist in understanding the disclosure, and is not intended to be limiting.

The figures illustrating the dual chamber syringe system of the invention (hereinafter "the system") show some mechanical elements that partially or fully resemble standard mechanical elements used in the art and that will be recognized by one skilled in the art. The detailed descriptions of these elements are presented herein only to the degree necessary to facilitate an understanding of the novel features of the present invention.

Referring to FIG. 1, the system is designated generally therein by the reference number 100. The system 100 comprises several primary mechanical components, described hereinafter. The system includes a first cylindrical container (or barrel) 10 defining a first chamber 11. As further illustrated in FIG. 2A, first container 10/chamber 11 mostly resemble the main body of a standard syringe, including a first open end 12 and nozzle (or tip) 13 for dispensing that are narrower than the main body of the syringe, and wherein the nozzle 13 may be fitted with a standard detachable hypodermic needle 14. As contemplated herein, it is to be understood that nozzle 13 may alternatively be fitted with any of a variety of other standard needles or tubing (not shown) as typically used, e.g., in medical settings. It is also to be understood that nozzle 13 may be in the form of any of a variety of commonly known syringe tips, such as, illustratively, the type commonly known as a slip tip, the type commonly known as a catheter tip, or the type commonly known as a Luer Lock tip. Additionally, it is to be understood that an obvious variation is the tip commonly known as an eccentric tip (not shown), where the open end 12/nozzle 13 are not positioned in the center but at the side of the barrel.

Referring again to FIG. 1 and FIG. 2A, first container 10 further includes on the opposite end of the barrel a second open end 15 having a diameter equal to that of the barrel, and a flange 16 that includes an internal, i.e., female, thread 17 sized so that the diameter of the thread is greater than the diameter of the barrel. FIG. 2B illustrates the view of the first container 10/first chamber 11 looking straight into the second open end 15/flange 16 and down into the barrel.

It is to be understood that when the hypodermic needle 14 is not attached to first container 10, i.e., at the nozzle 13, if needed, the nozzle 13 may be capped with any one of the various types of syringe caps known in the art, many of which are commercially available. Likewise, when the hypodermic needle 14 is attached to first container 10, i.e., at the nozzle 13, then needle 14 may be shielded with any one of the various types of commercially available needle shields known in the art.

First container 10 may be manufactured of any of the standard plastic or glass materials customarily used in making syringes, and may preferably be transparent, but may also be semi-transparent or translucent. It is also conceivable that in certain specialized applications the container may need to be opaque. Also, first container 10 may optionally include scale markings or graduations on the outer wall to allow accurate and visual measurement of its contents.

Figure 3B:
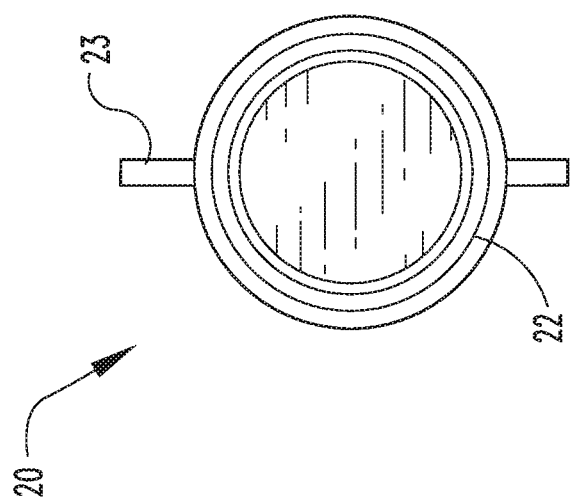
FIG. 3B is a cross-sectional view of the male end cap looking down the front end.

Referring now to FIG. 1 and FIG. 3A, the system 100 also comprises a cap 20, which is designed for the purpose of sealing the first container 10 at the threaded flange 16. Cap 20 comprises a tip 21 that includes an outer, i.e., male, thread 22 precisely sized so as to screwably attach to flange 16 at the female thread 17. Also, cap 20 may optionally include a wing tip 23 to facilitate screwing the cap 20 onto flange 16. FIG. 3B illustrates the view of the cap 20 looking straight into the tip 21. Alternatively, instead of cap 20, the system 100 comprises a membrane (not shown) for the purpose of sealing the first container 10 at open end 15.

Cap 20 may be manufactured of any of the standard plastic, rubber or other materials customarily used in making syringe caps. In one variation of the invention herein, if needed, it is contemplated that cap 20 may also be fitted at the base of the tip 21 with a rubber O-ring of proper size, in order to ensure a tight seal when the cap 20 is screwed onto flange 16.

Referring now to FIG. 1 and FIG. 4A, the system 100 also comprises a second cylindrical container (or barrel) 30, defining a second chamber 31, wherein the internal diameter of the second chamber 31 is equal to the internal diameter of the first chamber 11. As illustrated in FIG. 4A, second container 30/chamber 31 mostly resemble the main body of a standard syringe, but lack the narrow dispensing nozzle of a standard syringe. Thus, second container 30/chamber 31 include a first open end 32 having the same internal diameter as that of the rest of chamber 31. Additionally, second container 30 is constructed to include in proximity with open end 32 an outer, i.e., male, thread 33, which is precisely sized so as to screwably attach tightly to flange 16 at female thread 17 of first container 10. It is to be understood that, as contemplated herein, when first container 10 and second container 30 are attached via screwing together female thread 17 and male thread 33, chamber 11 and chamber 31 become aligned cylindrically along the same axis.

Referring again to FIG. 1 and FIG. 4A, second container 30 further includes on the opposite end of the barrel a second open end 34 having the same internal diameter as that of the rest of chamber 31. As illustrated in FIG. 4A, second container 30 may optionally include in proximity with second open end 34 an outward protruding flange 35, which resembles the typical flange on a standard syringe. FIG. 4B illustrates the view of the second container 30/second chamber 31 looking straight into the second open end 34 and down into the barrel.

Second container 30 may be manufactured of any of the standard plastic or glass materials customarily used in making syringes, and may preferably be transparent, but may also be semi-transparent or translucent. It is also conceivable that in certain specialized applications the container may need to be opaque. Also, second container 30 may optionally include scale markings or graduations on the outer wall to allow accurate and visual measurement of its contents.

Figure 5B:
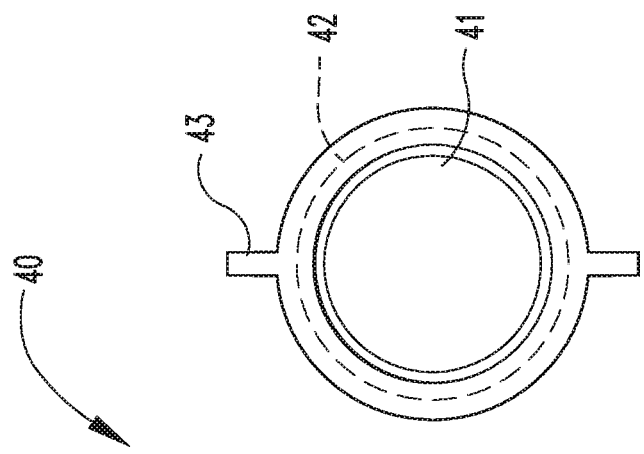
FIG. 5B is a cross-sectional view of the female end cap looking into the cavity.
Figure 5A:
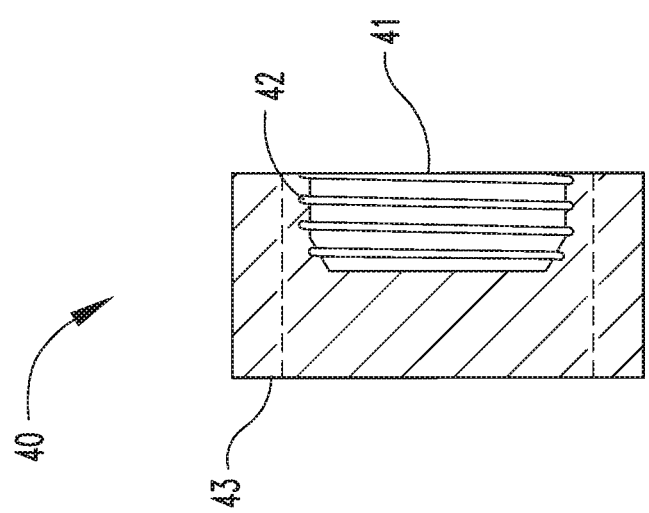
FIG. 5A is a longitudinal cross-sectional view of the female end cap of the second chamber.

Referring now to FIG. 1 and FIG. 5A, the system 100 also comprises a cap 40, which is designed for the purpose of sealing the second container 30 at open end 32 via thread 33. Cap 40 comprises an inner cylindrical cavity 41 that includes a female thread 42 precisely sized so as to screwably attach to second container 30 at male thread 33. Also, cap 40 may optionally include a wing tip 43 to facilitate screwing the cap 40 onto male thread 33. FIG. 5B illustrates the view of the cap 40 looking straight into the cavity 41. Alternatively, instead of cap 40, the system 100 comprises a membrane (not shown) for the purpose of sealing the second container 30 at the open end 32.

Cap 40 may be manufactured of any of the standard plastic, rubber or other materials customarily used in making syringe caps. In one variation of the invention herein, if needed, it is contemplated that cap 40 may also be fitted at the base of the female thread 42 with a rubber O-ring of proper size, in order to ensure a tight seal when the cap 40 is screwed onto second container 30.

Figure 6A:
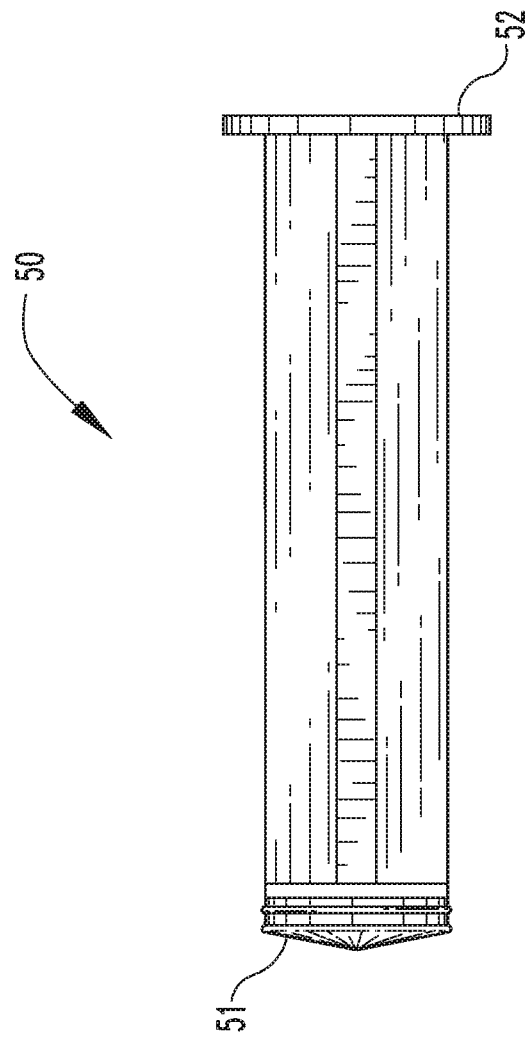
FIG. 6A is a longitudinal cross-sectional view of the plunger.
Figure 6B:
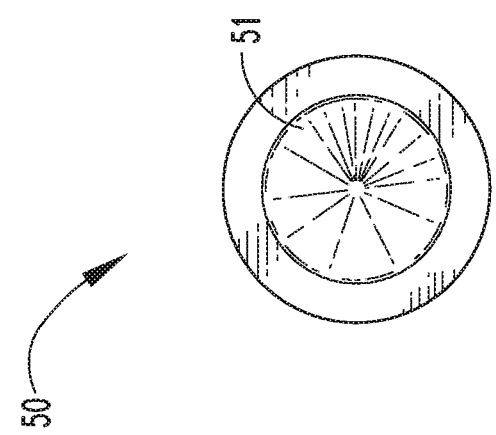
FIG. 6B is a cross-sectional view looking down the front end of the plunger.

Referring now to FIG. 1 and FIG. 6A, the system 100 also comprises a plunger (or piston) 50. Plunger 50 resembles a standard syringe plunger, and is designed to fit precisely, sealingly, and slidably into chamber 31 of second container 30 at open end 34, as well as into chamber 11 of first container 10 at open end 15. Additionally, the axial length of plunger 50 is sized to be longer than the combined axial lengths of chamber 11 and chamber 31 when container 10 and container 30 are attached together via threads 17 and 33, so that when plunger 50 is pressed, it can reach all the way through the length of the combined chambers. Plunger 50 includes a sealing ring 51 on the front end and may include a thumb press 52 on the back end. FIG. 6B illustrates the view of plunger 50 looking axially straight at its front end. It is to be understood that, as contemplated herein, the plunger can be manufactured of any one or a combination of plastic, rubber, glass, or any other standard material used in the art for making syringe plungers. It is also to be understood that, as contemplated herein, any of the alternative standard plunger designs known in the art may be used, provided that a good seal is achieved between plunger and barrel upon sliding the plunger into either chamber or the combined chambers. One type of seal commonly used at the front end of the plunger is a latex-free stopper that prevents leakage of medication around the plunger.

FIG. 7 shows first container 10 with needle 14 attached at nozzle 13, with second container 30 screwed on via female thread 17 and male thread 33, and plunger 50 inserted and slid/depressed through chamber 31 and partially into chamber 11.

It is to be understood that, as contemplated herein, an alternative arrangement of the foregoing system would be to reverse the threads by designing the first container 10 to include a male threaded opening instead of a female one and the second container 30 to include a female threaded opening instead of a male one.

In one embodiment of the dual chamber syringe system herein, first container 10 is fitted at nozzle 13 with a hypodermic needle 14, which is shielded and/or capped with a needle tip cap, and the container is filled via open end 15 with an accurately measured amount of a first medication; then it is sealed at female thread 17 with a male-threaded cap 20 or with a membrane. Alternatively, first container 10 is capped at nozzle 13 with a syringe tip cap. Likewise, second container 30 is sealed at its unthreaded end by inserting plunger 50 and sliding it part way into chamber 31 to the desired depth, and is filled via open end 32 with an accurately measured amount of a second medication; then it is sealed at male thread 33 with a female-threaded cap 40 or with a membrane. Subsequently, the foregoing assembled parts, containing the first and second medications, are packaged for storage and/or shipping using any of the standard packaging methods employed in the art. In one aspect of the invention, some or all of the foregoing steps are performed under sterile conditions, as deemed appropriate depending on the types of medications contained and/or the intended medical procedures. In an alternative embodiment, it is contemplated herein that the assembled sealed container containing the first medication and the assembled sealed container containing the second medication may be packaged separately for storage and/or shipping.

In another embodiment of the invention, provided herein is a kit that comprises the pre-assembled and pre-packaged parts as described in the preceding paragraph.

In another embodiment of the invention, a method of use of the dual chamber syringe system or the kit described above is disclosed. The method of use comprises the steps of removing the packaging, unscrewing the male and female caps, screwing together the first and second containers at the threaded ends, and removing the needle shield, thus rendering the dual chamber system ready for injection following standard medical procedures. Alternatively, if the first container had been sealed with a tip cap instead of a needle, the tip cap is removed, and a needle is attached prior to use. Also alternatively, if the containers had been sealed with membranes instead of the male and female caps, then connecting the containers by screwing them together would rupture the membranes resulting in mixing of the medications, thus rendering the dual chamber system ready for injection following standard medical procedures.

As contemplated herein throughout, in the foregoing and in the following, it is understood that when membranes are used to seal the containers said membranes should preferably be impermeable. However, it is also understood that, in certain specialized cases, the membranes may be selected from materials that are permeable to gas, but not to liquids or solids, if needed.

Any of a variety of suitable, commercially available membranes may be used to seal the containers. Illustratively, an impermeable membrane made of polytetrafluoroethylene (ePTFE), and developed by W. L. Gore & Associates, Inc., may be used. Thus, this impermeable membrane may be fastened to each chamber opening by stretching the membrane over the open ends of the containers. The membranes will remain fully intact until the containers are connected.

In another embodiment, disclosed herein is a modular, pre-fillable dual chamber syringe system for administering medications to a patient by injection, comprising: (a) a first, plungerless syringe container comprising a cylindrical hollow body of uniform diameter that includes on one end a nozzle suitable for fitting a needle for injection and on the other end a female-threaded connector; (b) a means to seal the first container at the female-threaded connector; (c) a second syringe container comprising a cylindrical hollow body of uniform diameter equal to the diameter of the first syringe container, and includes a first open end with a male-threaded connector precisely sized to screwably connect to the female-threaded connector of the first syringe container, and a second open end fitted with a syringe plunger, wherein the length of the plunger is longer than the combined length of the first syringe container and the second syringe container when screwed together; and, (d) a means to seal the second container at the male-threaded connector. In one aspect, the means to seal the first container is selected from the group consisting of a male-threaded cap and a membrane. Illustratively, when a membrane is used, it may be an impermeable membrane. In another aspect, the means to seal the second container is selected from the group consisting of a female-threaded cap and a membrane. Illustratively, when a membrane is used, it may be an impermeable membrane.

In another embodiment, disclosed herein is a method of use of a modular syringe system in accordance with the foregoing, said method comprising the steps of: (a) fitting the first syringe container at the nozzle with a needle and needle seal cap; (b) placing a measured amount of one or more medications into the first syringe container; (c) sealing the first syringe container at the female-threaded connector by using a sealing means; (d) partially sliding the plunger into the second container to a desirable depth; (e) placing a measured amount of one or more medications into the second container; (f) sealing the second container at the male-threaded connector by using a sealing means; (g) packaging under sterile conditions the sealed first container and the sealed second container; (h) storing the package obtained in (g) above until needed for use; (i) removing the packaging from the package obtained in (g) above; (j) connecting the first container and second container by screwing the female-threaded connector and the male-threaded connector together; (k) removing the needle seal cap; (l) injecting the medications contained in the dual chamber system into a patient by pushing the plunger. In one aspect, the one or more medications in the first container and the one or more medications in the second container are different from each other. In another aspect, the means of sealing the first syringe container at the female-threaded connector is selected from the group consisting of a male-threaded cap and a membrane, and the means of sealing the second syringe container at the male-threaded connector is selected from the group consisting of a female-threaded cap and a membrane. Illustratively, when membranes are used, they may be impermeable membranes. In another aspect, when the first container and the second container are screwed together, the membranes are ruptured and the medications in the first container and the second container are mixed.

In another embodiment, disclosed herein is a modular dual chamber syringe kit comprising the dual chamber syringe system in accordance with the foregoing, said kit further comprising: (a) one or more medications pre-charged into the first container that is sealed at the female-threaded connector with a sealing means and capped at the nozzle with a capping means selected from the group consisting of a tip cap and a needle fitted with a needle seal cap; and, (b) one or more medications pre-charged into the second container that is sealed at the male-threaded connector with a sealing means. In one aspect, the kit further comprises a package enclosing the sealed first container and the sealed second container under sterile conditions. In another aspect, the sealing means of the first syringe container at the female-threaded connector is selected from the group consisting of a male-threaded cap and a membrane, and the sealing means of the second syringe container at the male-threaded connector is selected from the group consisting of a female-threaded cap and a membrane. Illustratively, when membranes are used, they may be impermeable membranes.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. It is understood that additions, omissions, substitutions, and other modifications can be made by those skilled in the art without departing from the scope of the present invention.

What claimed is:

1. A modular, pre-fillable dual chamber syringe system for administering medications to a patient by injection, comprising:
   (a) a first, plungerless syringe container comprising a cylindrical hollow body of uniform diameter that includes on one end a nozzle suitable for fitting a needle for injection and on the other end a female-threaded connector;
   (b) a means to seal the first container at the female-threaded connector;
   (c) a second syringe container comprising a cylindrical hollow body of uniform diameter equal to the diameter of the first syringe container, and includes a first open end with a male-threaded connector precisely sized to screwably connect to the female-threaded connector of the first syringe container, and a second open end fitted with a syringe plunger, wherein the length of the plunger is longer than the combined length of the first syringe container and the second syringe container when screwed together; and,
   (d) a means to seal the second container at the male-threaded connector.

2. The system of claim 1 wherein the means to seal the first container is selected from the group consisting of a male-threaded cap and a membrane.

3. The system of claim 2 wherein the means to seal the first container is a membrane.

4. The system of claim 3 wherein the membrane is impermeable.

5. The system of claim 1 wherein the means to seal the second container is selected from the group consisting of a female-threaded cap and a membrane.

6. The system of claim 5 wherein the means to seal the second container is a membrane.

7. The system of claim 6 wherein the membrane is impermeable.

8. A method of use of a modular syringe system in accordance with claim 1, said method comprising the steps of:
   (a) fitting the first syringe container at the nozzle with a needle and needle seal cap;
   (b) placing a measured amount of one or more medications into the first syringe container;
   (c) sealing the first syringe container at the female-threaded connector by using a sealing means;
   (d) partially sliding the plunger into the second container to a desirable depth;
   (e) placing a measured amount of one or more medications into the second container;
   (f) sealing the second container at the male-threaded connector by using a sealing means;
   (g) packaging under sterile conditions the sealed first container and the sealed second container;
   (h) storing the package obtained in (g) above until needed for use;
   (i) removing the packaging from the package obtained in (g) above;
   (j) connecting the first container and second container by screwing the female-threaded connector and the male-threaded connector together;
   (k) removing the needle seal cap; and,
   (l) injecting the medications contained in the dual chamber system into a patient by pushing the plunger.

9. The method of claim 8 wherein the one or more medications in the first container and the one or more medications in the second container are different from each other.

10. The method of claim 8 wherein the means of sealing the first syringe container at the female-threaded connector is selected from the group consisting of a male-threaded cap and a membrane, and the means of sealing the second syringe container at the male-threaded connector is selected from the group consisting of a female-threaded cap and a membrane.

11. The method of claim 10 wherein the means of sealing of both of the first and second containers are membranes.

12. The method of claim 11 wherein the membranes are impermeable.

13. The method of claim 11 wherein, when the first container and the second container are screwed together, the membranes are ruptured and the medications in the first container and the second container are mixed.

14. A modular dual chamber syringe kit comprising the dual chamber syringe system in accordance with claim 1, said kit further comprising:
   (a) one or more medications pre-charged into the first container that is sealed at the female-threaded connector with a sealing means and capped at the nozzle with a capping means selected from the group consisting of a tip cap and a needle fitted with a needle seal cap; and,
   (b) one or more medications pre-charged into the second container that is sealed at the male-threaded connector with a sealing means.

15. The kit of claim 14 further comprising a package enclosing the sealed first container and the sealed second container under sterile conditions.

16. The kit of claim 14 wherein the sealing means of the first syringe container at the female-threaded connector is selected from the group consisting of a male-threaded cap and a membrane, and the sealing means of the second syringe container at the male-threaded connector is selected from the group consisting of a female-threaded cap and a membrane.

17. The kit of claim 16 wherein the sealing means of both of the first and second containers at their respective threaded connectors are membranes.

18. The kit of claim 17 wherein the membranes are impermeable.

19. The kit of claim 14 wherein the nozzle capping means is a tip cap.

20. The kit of claim 14 wherein the nozzle capping means is a needle fitted with a needle seal cap.

* * * * *